(12) United States Patent
Francis

(10) Patent No.: US 7,691,400 B2
(45) Date of Patent: Apr. 6, 2010

(54) MEDICAL DEVICE HAVING COATING WITH ZEOLITE DRUG RESERVOIRS

(75) Inventor: Richard Francis, White Bear Lake, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 922 days.

(21) Appl. No.: 11/381,823

(22) Filed: May 5, 2006

(65) Prior Publication Data

US 2007/0259017 A1 Nov. 8, 2007

(51) Int. Cl.
 *A61F 2/00* (2006.01)
 *A61F 2/06* (2006.01)
 *C01B 39/00* (2006.01)

(52) U.S. Cl. ........................ 424/423; 623/1.42; 423/700

(58) Field of Classification Search ........................ None
 See application file for complete search history.

(56) References Cited

U.S. PATENT DOCUMENTS

| | | | |
|---|---|---|---|
| 4,733,665 A | 3/1988 | Palmaz | |
| 4,739,762 A | 4/1988 | Palmaz | |
| 4,800,882 A | 1/1989 | Gianturco | |
| 4,886,062 A | 12/1989 | Wiktor | |
| 5,133,732 A | 7/1992 | Wiktor | |
| 5,292,331 A | 3/1994 | Boneau | |
| 5,314,472 A | 5/1994 | Fontaine | |
| 5,334,368 A | 8/1994 | Beck et al. | |
| 5,336,665 A | 8/1994 | Garner-Gray et al. | |
| 5,421,955 A | 6/1995 | Lau et al. | |
| 5,776,161 A | 7/1998 | Globerman | |
| 5,817,152 A | 10/1998 | Birdsall et al. | |
| 5,913,897 A | 6/1999 | Corso et al. | |
| 5,935,162 A | 8/1999 | Dang | |
| 6,019,784 A | 2/2000 | Hines | |
| 6,027,528 A | 2/2000 | Tomonto et al. | |
| 6,090,127 A | 7/2000 | Globerman | |
| 6,113,627 A | 9/2000 | Jang | |
| 6,114,049 A | 9/2000 | Richter | |
| 6,245,732 B1 | 6/2001 | Gallon et al. | |
| 6,379,383 B1 | 4/2002 | Palmaz et al. | |
| 6,419,693 B1 | 7/2002 | Fariabi | |
| 6,423,411 B2 | 7/2002 | Balkus, Jr. et al. | |
| 6,436,422 B1 * | 8/2002 | Trogolo et al. | ............... 424/405 |
| 6,663,661 B2 | 12/2003 | Boneau | |
| 6,730,116 B1 | 5/2004 | Wolinsky et al. | |
| 6,865,810 B2 | 3/2005 | Stinson | |
| 6,866,805 B2 | 3/2005 | Hong et al. | |
| 6,932,959 B2 | 8/2005 | Sterte et al. | |
| 2002/0004060 A1 | 1/2002 | Heublein et al. | |
| 2003/0059640 A1 | 3/2003 | Marton et al. | |
| 2004/0158314 A1 | 8/2004 | Hogendijk | |
| 2004/0186556 A1 | 9/2004 | Hogendijk et al. | |
| 2005/0060020 A1 | 3/2005 | Jenson | |
| 2005/0071016 A1 | 3/2005 | Hausdorf et al. | |
| 2005/0090888 A1 | 4/2005 | Hines et al. | |
| 2005/0098241 A1 | 5/2005 | Wachter et al. | |
| 2008/0003256 A1 * | 1/2008 | Martens et al. | ............. 424/425 |

FOREIGN PATENT DOCUMENTS

| | | |
|---|---|---|
| DE | 137599 | 9/1979 |
| DE | 248508 | 8/1987 |
| EP | 535942 | 4/1993 |
| EP | 536942 | 4/1993 |
| WO | WO 94/28107 | 12/1994 |
| WO | WO 00/32273 | 6/2000 |
| WO | WO 00/64506 | * 11/2000 |
| WO | WO00/64506 | 11/2000 |
| WO | WO 03/094735 | 11/2003 |
| WO | WO 2004/108346 | 12/2004 |
| WO | WO 2005/013856 | 2/2005 |
| WO | WO 2005/025453 | 3/2005 |
| WO | WO 2005/026399 | 3/2005 |
| WO | WO 2005/044361 | 5/2005 |
| WO | WO2006/002498 | 1/2006 |

\* cited by examiner

*Primary Examiner*—Jean C. Witz
*Assistant Examiner*—Raymond P Yeager

(57) ABSTRACT

A medical device having a drug-eluting coating that includes a pharmaceutical compound or, more generally, a therapeutic material housed within pores of a zeolite carrier. The zeolite carrier has an open porous structure with reservoirs for holding the therapeutic material. The therapeutic material loaded zeolites may be suspended or dispersed within a bioerodible polymer matrix to provide controlled delivery of the therapeutic material. Zeolite drug carriers may have enhanced or optimally engineered pore sizes for a particular therapeutic material and release profile. Along with a therapeutic material, reservoirs of a zeolite drug delivery system may include a release agent. The release agent may be used to entrap the therapeutic material until such time as a triggering condition is met that prompts the release agent to activate and thereby release the therapeutic material from the zeolite reservoir.

18 Claims, 2 Drawing Sheets

MEDICAL DEVICE HAVING COATING WITH ZEOLITE DRUG RESERVOIRS

FIELD OF THE INVENTION

The present invention relates generally to a drug-eluting coating for a medical device. More particularly, the present invention is directed to a coating for an implantable medical device, such as stents and grafts, that contains zeolite drug reservoirs for releasing a therapeutic material after implantation in a patient's vessel.

BACKGROUND OF THE INVENTION

Prosthetic devices, such as stents or grafts, may be implanted during interventional procedures such as balloon angioplasty to reduce the incidence of vessel restenosis. To improve device effectiveness, implantable medical devices may be coated with one or more therapeutic agents providing a mode of localized drug delivery. The therapeutic agents are typically intended to limit or prevent restenosis. For example, anti-thrombogenic agents such as heparin or clotting cascade IIb/IIIa inhibitors (e.g., abciximab and eptifibatide) may be coated on the stent, thereby diminishing thrombus formation. Such agents may effectively limit clot formation at or near the implanted device. Some anti-thrombogenic agents, however, may not be effective against intimal hyperplasia. Therefore, the implantable medical device may also be coated with anti-proliferative agents or other compounds to reduce excessive endothelial re-growth. Therapeutic agents provided as coating layers on implantable medical devices may effectively limit restenosis and reduce the need for repeated treatments. Therapeutic agents that provide other benefits, such as anti-plaque agents, e.g., naproxen and ibuprofen, also be may desirably coated onto an implantable medical device.

Several strategies have been developed for coating one or more therapeutic agents onto the surface of an implantable medical devices. Standard methods may include dip coating, spray coating, and chemical bonding. The therapeutic agent coating may be applied as a mixture, solution, or suspension of polymeric material and/or drugs dispersed in an organic vehicle or a solution or partial solution. However, the creation of an implantable medical device coating such that a drug may be delivered in a reliable but controlled manner presents many challenges, particularly the need to dissolve the drug inside the polymer carrier. Such drug dissolution often requires the use of solvents to dissolve the drug, and further solvents or co-solvents to dissolve the polymer. As such, finding the right solvents with the right polymer to deliver the right drug can be difficult to achieve. What is needed is a drug-eluting polymeric coating for an implantable medical device that does not require the use of co-solvents between the drug and the polymer carrier.

Hydrophilic polymeric coatings containing antibiotic zeolites known in the art may provide one solution to this problem. The antibiotic zeolites are created by an ion-exchange process wherein antibiotic metal ions; such as, silver, copper or zinc ions, are retained on zeolite particles through an ion exchange reaction. The antibiotic zeolites are dispersed in a hydrophilic polymer, for example, by high shear mixing, and the hydrophilic polymer is then dissolved in an organic solvent to provide a coating solution for a medical article. Such an antibiotic hydrophilic polymer coating is disclosed in U.S. Pat. No. 6,436,422 to Trogolo et al., which is incorporated by reference herein in its entirety. However, a need still exists for a drug-eluting polymeric coating for an implantable medical device with a controlled dosing profile that can be used to deliver a greater variety of therapeutic agents and that does not require the use of co-solvents between the therapeutic agent and the polymer carrier.

BRIEF SUMMARY OF THE INVENTION

An embodiment according to the present invention is a medical device having at least one surface for contacting a bodily tissue, organ or fluid having a substrate with a contacting surface; and a drug-eluting coating on at least a portion of the contacting surface. The drug-eluting coating includes a polymer having zeolites dispersed there through, wherein a porous structure of the zeolites includes reservoirs containing a release agent and a therapeutic material. In an embodiment, the release agent prevents the therapeutic material from exiting the reservoir until a triggering condition is met, wherein the triggering condition may be contact of the release agent with a bodily fluid or a change in pH proximate the release agent. The polymer coating may be bioerodible.

Another embodiment according to the present invention is a drug-eluting stent for implanting in a body lumen having a radially expandable stent structure and a coating on at least a portion of a surface of the stent structure. The coating includes a polymer having zeolites dispersed there through, wherein a porous structure of the zeolites includes reservoirs containing a therapeutic material. In an embodiment, the reservoirs may also contain a release agent for preventing the release of the therapeutic material from the reservoir until a triggering condition is met, such as contact of the release agent with a bodily fluid or a change in pH proximate the release agent. In a further embodiment, the coating polymer is a bioerodible polymer having lactic acid as a degradation product for providing a change in pH as the triggering condition.

A therapeutic coating according to an embodiment of the present invention may include an outer layer having zeolites containing a first pharmaceutical compound and an inner layer having zeolites containing a second pharmaceutical compound. In such an embodiment, the outer coating layer may be of a bioerodible polymer and the first pharmaceutical compound may be selected from an anti-coagulant drug and/or an anti-inflammatory drug. Further, the inner coating layer may include the second pharmaceutical compound being an anti-proliferative and/or a pro-healing agent to promote rapid re-endothelialization.

Another embodiment according to the present invention is a drug-eluting coating for a medical device having a polymer dispersed with zeolite drug carriers, wherein a porous structure of the zeolite drug carriers includes reservoirs containing a pharmaceutical compound. In an embodiment, the coating may include an outer layer of a bioerodible polymer having zeolite drug carriers with a first pharmaceutical compound and an inner layer of a polymer matrix having zeolite drug carriers with a second pharmaceutical compound.

BRIEF DESCRIPTION OF DRAWINGS

The foregoing and other features and advantages according to the invention will be apparent from the following description as illustrated in the accompanying drawings. The accompanying drawings, which are incorporated herein and form a part of the specification, further serve to explain the principles according to the invention. The drawings are not to scale.

DETAILED DESCRIPTION OF THE INVENTION

Figure 1:
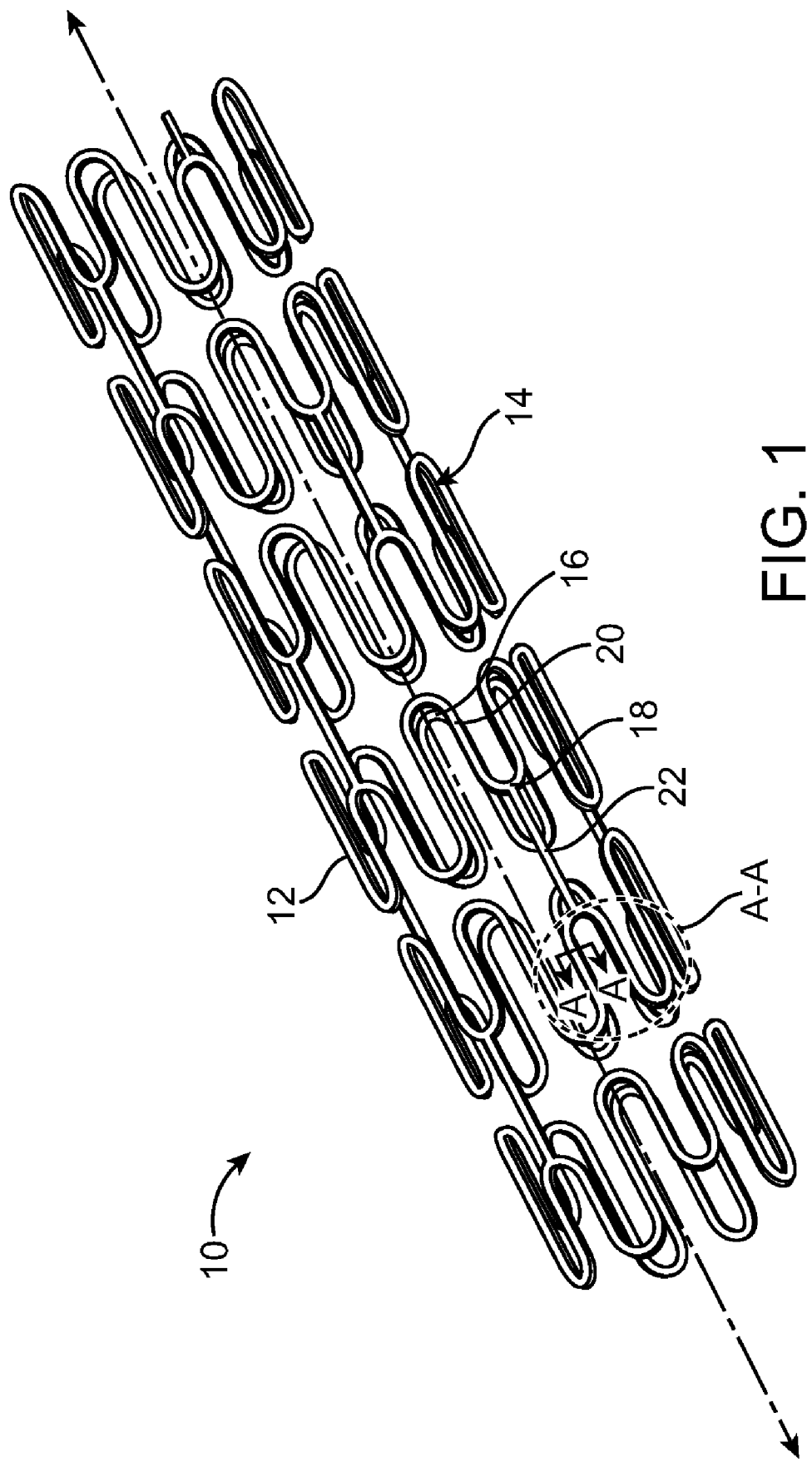
FIG. 1 a perspective view of an exemplary stent in accordance with an embodiment of the present invention.

An embodiment according to the present invention is a drug-eluting stent in which a pharmaceutical compound or, more generally, a therapeutic material is housed within the pores of a zeolite carrier. Aluminosilicates, e.g., zeolites, are crystalline porous nanostructures with long range crystalline order having pore sizes which can be varied from about 4 Å to 15 Å in conventional zeolites. Zeolites may possess a 3-dimensional, e.g., MFI, zeolite cage structure with straight and ziz-zag channels or may be a 2-dimensional zeolite with channels only in 2 directions. Thus, a variety of zeolites have an open porous structure that provides channels or "reservoirs" for a therapeutic material. Zeolites housing a therapeutic material may be suspended or dispersed within a polymer carrier to be coated on a surface of a medical device to thereby provide controlled delivery of the therapeutic material. An embodiment according to the present invention includes zeolites that have enhanced or optimally engineered pore sizes for housing a particular pharmaceutical compound and providing a desirable drug release profile therefor.

Suitable zeolites may be found in natural form or synthesized in discrete and continuous forms, and may be either isotropic or anisotropic in nature. In an embodiment, zeolites may be synthesized such that they are directionally grown and thus have enhanced drug delivery characteristics. For instance, a zeolite may be deposited by laser ablation on a stent substrate and subjected to a hydrothermal treatment as disclosed in U.S. Pat. No. 6,423,411 B2 to Balkus, Jr. et al., which is incorporated by reference herein in its entirety. Zeolite crystals formed by this process may be plank-like and oriented normal to the substrate surface with parallel channels therebetween. The channels may be used to hold a therapeutic material within the zeolite structure. In another embodiment, zeolites may be synthesized to hold a therapeutic material such that the drug-filled zeolites may then be dispersed as discrete units in a polymeric vehicle or matrix.

In another embodiment, a zeolite drug carrier includes a release agent, wherein the release agent entraps a deliverable agent, i.e., a pharmaceutical compound or a therapeutic material, until such time as a triggering condition is met. The triggering condition promotes the release agent to activate and to release the deliverable agent from the zeolite reservoir making it bioavailable. In an embodiment, a release agent may be chosen from any of the biodegradable polymers listed below, wherein the triggering condition may be hydrolysis-driven or pH-driven.

A controlled-release system according to another embodiment of the present invention may rely on diffusion of a therapeutic material through a selectively permeable diffusion barrier, thereby obviating the use of bioerodible systems. A diffusionally controlled system may include a core coating layer on a surface of a stent that includes a zeolite containing a bioactive agent. The core layer may then be surrounded by an inert diffusion barrier as a second or outer polymeric coating layer. As in the zeolite drug reservoir systems, drug diffusion through the polymer matrix, i.e., the polymeric diffusion layer is the rate-limiting step, and release rates are determined by the selection of polymer, the polymer's effect on the diffusion of the therapeutic material, and a partition coefficient of the therapeutic material to be released.

In a chemically controlled system according to another embodiment of the present invention, chemical control can be achieved using bioerodible or pendant chains. Polymer bioerosion can be defined as the conversion of a material that is insoluble in water into one that is water-soluble. A bioerodible polymer may be used to encapsulate a zeolite loaded with a therapeutic material such that as it erodes it allows the therapeutic agent to escape from the zeolite reservoir.

In a solvent-activated controlled system according to another embodiment of the present invention, the active or therapeutic agent is initially held within the zeolite reservoir and encapsulated within a polymeric shell and is not able to diffuse through that shell, until such time that it is placed in an in vivo environment, where fluid (e.g., water) penetrates the shell swelling the polymer and lowering its glass transition temperature below the environmental, viz. host, temperature. Thus, the swollen polymer is in a rubbery state and allows the drug contained within the zeolite reservoir to diffuse out through the polymeric shell.

Embodiments according to the present invention are not limited by the nature of the medical device, rather, a wide variety of medical devices may benefit from a coating layer that includes zeolite drug reservoirs according to embodiments of the present invention. Thus, as used herein, the term "medical device" refers generally to any device that has at least one surface that can, in the ordinary course of its use and operation, contact bodily tissue, organs or fluids, such as blood. Examples of medical devices include, without limitation, stent guides, needles, guidewires, surgical instruments, angioplasty balloons, wound drains, tubing, urethral inserts, pellets, implants, pumps, and the like. A medical device can be an extracorporeal device, such as a device used during surgery that includes, for example, a blood oxygenator, blood pump, blood sensor, or tubing used to carry blood, and the like, which contact blood that is then returned to the subject. A medical device can likewise be an implantable device, such as, a vascular graft, stent, stent graft, anastomotic connector, electrical stimulation lead, heart valve, orthopedic device, catheter, shunt, sensor, pacemaker, replacement device for nucleus pulposus, cochlear or middle ear implant, intraocular lens, and the like. Implantable devices include transcutaneous devices, such as drug injection ports and the like.

FIG. 1 illustrates an exemplary medical device on which a zeolite drug carrier system, viz., zeolite drug reservoirs, may be utilized in accordance with an embodiment of the present invention. Stent 10 is a patterned tubular device that includes a plurality of radially expandable cylindrical rings 12. Cylindrical rings 12 are formed from struts 14 formed in a generally sinusoidal pattern including peaks 16, valleys 18, and generally straight segments 20 connecting peaks 16 and valleys 18. Connecting links 22 connect adjacent cylindrical rings 12 together. In FIG. 1, connecting links 22 are shown as generally straight links connecting peak 16 of one ring 12 to valley 18 of an adjacent ring 12. However, connecting links 22 may connect a peak 16 of one ring 12 to a peak 16 of an adjacent ring, or a valley 18 to a valley 18, or a straight segment 20 to a straight segment 20. Further, connecting links 22 may be curved. Connecting links 22 may also be excluded, with a peak 16 of one ring 12 being directly attached to a valley 18 of an adjacent ring 12, such as by welding, soldering, or the manner in which stent 10 is formed, such as by etching the pattern from a flat sheet or a tube. It will be appreciated by those of ordinary skill in the art that stent 10 of FIG. 1 is merely an exemplary stent and that stents of various forms and methods of fabrication can be used in accordance with various embodiments of the present invention. For example, in a typical method of making a stent, a thin-walled, small diameter metallic tube is cut to produce the desired stent pattern, using methods such as laser cutting or chemical etching. The cut stent may then be de-scaled, polished, cleaned and rinsed. Some examples of methods of forming stents and structures for stents are shown in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,935,162 to Dang, U.S. Pat. No. 6,090,127 to Globerman, and U.S. Pat. No. 6,730,116 to Wolinsky et al., each of which is incorporated by reference herein in its entirety.

Figure 2A:
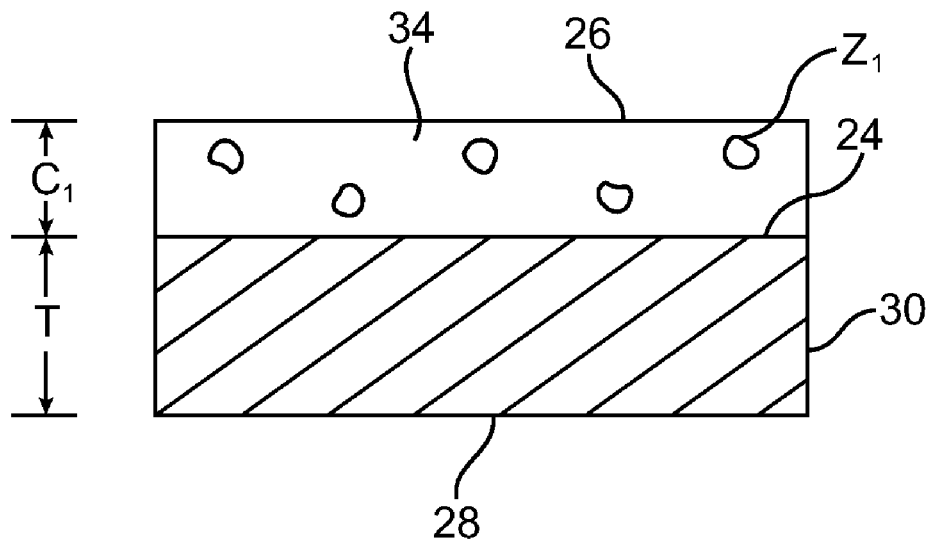
FIG. 2A is a schematic cross-sectional view of a stent strut taken along line A-A of FIG. 1 showing a coating in accordance with an embodiment of the present invention.

In the embodiment of FIG. 2A, coating 26 has a coating thickness $C_1$. Coating 26 is comprised of a biocompatible polymer 34 dispersed with a plurality of zeolite drug carriers $Z_1$, which house one or more therapeutic materials therein.

Figure 2B:
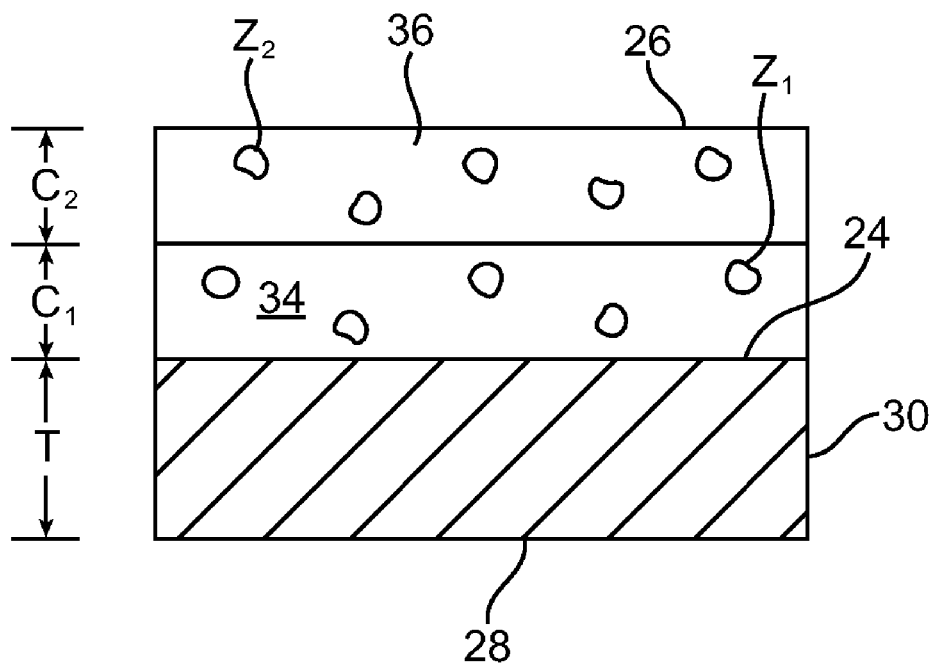
FIG. 2B is a schematic cross-sectional view of a stent strut taken along line A-A of FIG. 1 showing a coating in accordance with another embodiment of the present invention.

In the embodiment of FIG. 2B, coating 26 has an inner layer of a thickness $C_1$ and an outer layer of a thickness $C_2$. Coating layer $C_1$ is comprised of a biocompatible polymer 34 dispersed with a plurality of zeolite drug carrier $Z_1$, housing a first therapeutic material therein. Coating layer $C_2$ is comprised of a biocompatible polymer 36 dispersed with a plurality of zeolite drug carriers $Z_2$ housing a second therapeutic material therein. In various embodiments, polymers 34, 36 may be the same or different polymers, and may be biostable or bioerodible. In embodiments according to the present invention, zeolite drug carriers $Z_1$, $Z_2$ may be of the same or a different zeolite structure, and may have the same or a different pore size. Further, first and second therapeutic materials may be the same or a different material depending on the therapeutic effect and profile desired.

Further in each embodiment only outer surface 24 is shown coated by coating 26. However it should be understood that in various other embodiments, all or portions of outer surface 24, inner surface 28, and/or side surfaces 30 may be coated with coating 26, as may be desired to achieve various dosages of the therapeutic agent.

Typical materials used for stent 10 are metals or alloys, examples of which include, but are not limited to, stainless steel, "MP35N," "MP20N," nickel titanium alloys such as nitinol (e.g., ELASTINITE® by Advanced Cardiovascular Systems, Inc., Santa Clara, Calif.), tantalum, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The zeolite drug carrier system also may be used with any of the balloon-expandable stent designs disclosed in U.S. Pat. Nos. 5,776,161, 6,113,627, and 6,663,661, which are incorporated by reference herein in their entirety.

Zeolites are microporous crystalline solids with well-defined structures. Generally a zeolite contains silicon, aluminum and oxygen in its framework and cations, water and/or other molecules within its pores. Many zeolites occur naturally as minerals, others are synthetic. A commonly used description of a zeolite is a crystalline aluminosilicate with a cage structure. More particularly, a zeolite is described as a crystalline hydrated aluminosilicate whose framework structure encloses cavities (or pores) occupied by cations and water molecules, each of which has considerable freedom of movement that permits ion exchange and reversible ion adsorption/desorption. Zeolites are typically based on aluminosilicates and metal alumino silicate compounds possessing three dimensional skeletal-like structure, and may be represented by the general formula $XM_2/nO—Al_2O_3—YSiO_2—ZH_2O$, wherein M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of suitable zeolites include: A-type metal aluminosilicates, T-type, X-type and Y-type, high silica zeolites, sodalite, mordenite, analcite, clinoptilolite, chabazite and erionite. A-type zeolites are essentially non-toxic via oral, dermal, ocular, and respiratory routes of exposure and are also safe for the environment. Embodiments according to the present invention are not restricted to the use any of these specific zeolites. In an embodiment, an implantable medical device having a zeolite drug carrier coating utilizes an A-type zeolite as the drug reservoirs.

Zeolites are considered structurally stable. However, zeolite modification may be desirable and implies an irreversible change in the zeolite structure, unlike ion exchange or adsorption. There are a number of different ways that zeolites can be modified. The framework of the zeolite can be modified by synthesizing zeolites with metal cations other than aluminum and silicon in the framework. The framework of the zeolites can also be modified by dealumination to increase the silica and thereby increase the hydrophobic nature of the zeolite. There are many proprietary methods to modify zeolites that impart unique characteristics to them, which include permutations of novel chemistry, synthesis, and processing.

Zeolites are available as powders or as formed products such as extrudates. For use in various embodiments according to the present invention, the zeolites may be naturally occurring or synthetically manufactured. In accordance with embodiments of the present invention for implantation within a vessel system, the loading and size of a zeolite should be selected such that it will not promote microembolisms.

Zeolites possess a network of pores that are typically of a consistent fixed mean diameter depending upon the system. Embodiments according to the present invention may employ uniform pore sizes in the nano-scale, micro-scale, or meso-scale ranges. Accordingly, aluminosilicates, such as M41S, with pores sizes between 20 and 100 Å in diameter are suitable for housing certain therapeutic materials, particularly MCM-41, which consists of hexagonal arrays of uniform 2 to 10 nanometer-sized cylindrical pores. Other unique zeolite structures, such as "tubules-within-a-tubule" have been fabricated as mesoporous molecular sieves and may be suitable for embodiments of the present invention.

Other approaches to synthesizing large pore and large single crystals of zeolytic materials have yielded crystals as large as 5 mm. Zeolytic materials with large pore size are suitable for housing more than one therapeutic materials, or therapeutic materials of larger size and/or higher doses. The ability to synthesize zeolitic materials of precise pore size in the range between 4 and 100 Å increases the types and number of therapeutic materials, as well as therapies that may be achieved via zeolite delivery systems according to the present invention.

Zeolites having a combination of uniform porous structure and high adsorption capacity can selectively adsorb molecules, viz., to be used as molecular sieves. A variety of mesoporous molecular sieves have been synthesized using cationic surfactants to assemble silicate anions from solution. Mesoporous molecular sieves made in this manner include zeolites having very uniform hexagonal arrays of non-intersecting tubular pores, referred to as mesoporous hexagonal molecular sieves (HMS), which possess high surface areas, ordered frameworks, and narrow pore size distributions. The array of hexagonal pores can be tailored within a range of 2 to 10 nm, as well as larger sizes, by varying the synthesis conditions, such as by changing the length of the template molecule. In an embodiment according to the present invention, zeolites comprised of uniform, tubular hexagonal molecules having pore dimensions in the meso-scale range (diameter from 20 to 100 Å) are used as reservoirs to hold a pharmaceutical compound and/or other therapeutic agent, including biological agents and moieties. Processes for making porous inorganic materials, to include crystalline zeolites, with controlled size, shape and porosity are disclosed in U.S. Pat. No. 6,932,959 B2 to Sterte et al., which is incorporated by reference herein in its entirety.

Zeolites exhibit the characteristic of self-assembly, which means that novel and reproducible structures can be fabricated in industrially significant quantities. Zeolites according to the present invention may be synthesized/generated via self-assembly techniques whereby large molecular structures are then obtained from the organization of a large number of molecules or atoms into a suitable shape for drug delivery, typically through specific interactions of the molecules among themselves and with a zeolite drug-delivery template.

Zeolites according to embodiments of the present invention serve as drug reservoirs, or drug carriers, may be used to hold a wide variety of therapeutic agents/materials, wherein the pore size of the zeolite may be modulated to accommodate a particular therapeutic material. Active therapeutic materials can be synthetic or naturally occurring and include, without limitation, organic and inorganic chemical agents. Zeolite drug reservoirs according to various embodiments of the present invention may house any of the following therapeutic materials, alone or in combination: anti-proliferative agents, anti-inflammatory agents, cell suspensions, polypeptides which is used herein to encompass a polymer of L- or D-amino acids of any length including peptides, oligopeptides, proteins, enzymes, hormones and the like, immunesuppressants, monoclonal antibodies, polynucleotides which is used herein to encompass a polymer of nucleic acids of any length including oligonucleotides, single- and double-stranded DNA, single- and double-stranded RNA, iRNA, DNA/RNA chimeras and the like, saccharides, e.g., mono-, di-, poly-saccharides, and mucopolysaccharides, vitamins, viral agents, and other living material, radionuclides, and the like, antithrombogenic and anticoagulant agents, antimicrobial agents such as antibiotics, antiplatelet agents and antimitotics, i.e., cytotoxic agents, and antimetabolites.

According to various embodiments of the present invention, zeolite drug reservoirs/carriers are applied to the medical device in a polymer coating. In an embodiment, a suitable polymer acts like a matrix and may be either biostable or bioerodible. In embodiments utilizing bioerodible polymers, erosion, which may include surface and/or bulk degradation of the polymer coating, occurs over time to reveal more of the zeolite drug reservoirs. Accordingly, a drug elution profile may be controlled either by a continuous distribution of zeolite drug reservoirs within the polymer matrix or by a graded distribution of zeolite drug reservoirs in a layered polymer coating. A graded distribution of zeolite drug reservoirs may be achieved by employing zeolite reservoirs of a variety of different pore shapes and/or sizes that contain one or more therapeutic materials. In an embodiment of an implantable medical device, zeolites with the largest pore size are in an outer coating layer to make a therapeutic material or drug contained therein readily available upon implantation. In a further embodiment, a plurality of coating layers may be applied, wherein the pore size of the zeolite chosen for each layer gradually decreases from the outer layer to the innermost layer. Accordingly, a therapeutic material in each layer will be distributed over an appropriate time period after implantation to maximize the therapeutic benefit thereof.

In another embodiment of an implantable medical device, a bioerodible outer coating layer having zeolite drug carriers housing a first pharmaceutical compound may be applied over an inner coating layer containing zeolite drug carriers housing a second pharmaceutical compound. In this embodiment, the first pharmaceutical compound is available upon implantation, while the second pharmaceutical compound becomes available upon at least partial erosion of the outer layer. In an embodiment where the implantable medical device is a stent, the first pharmaceutical compound may be an anti-coagulant drug and/or an anti-inflammatory drug and the second pharmaceutical compound may be an anti-proliferative and/or a 'pro-healing' agent to promote rapid re-endothelialization and other aspects necessary for correct vessel functionality.

In embodiments in which the zeolite drug carrier system includes a hydrolysable or a pH controlled or triggered release agent, initially the release agent may entrap the deliverable agent, i.e., the pharmaceutical compound or therapeutic agent, within the zeolite until such time as the triggering condition is met. Such zeolite drug carrier systems comprise zeolites having pore size of at least 6 Angstroms (e.g., Zeolite X or Y), a therapeutic material, i.e., a deliverable agent, releaseably incorporated in the pores of the zeolite, and a polymeric matrix coated on the loaded zeolite comprising a water-soluble composition in which the therapeutic material is substantially insoluble. Upon activation of the release agent under the triggering condition, the deliverable agent is subsequently released from the zeolite reservoir making it bioavailable. In an embodiment, a graded distribution of one or more release agents may be utilized in a layered configuration allowing for additional control over selective release of the therapeutic material(s) housed within the zeolite carrier. In another embodiment, a bioerodible polymer is chosen having lactic acid as a degradation product. In such an embodiment, the lactic acid locally lowers the pH proximate the medical device to trigger a pH controlled release agent within the zeolite to release the entrapped therapeutic agent.

Polymer matrices according to embodiments of the present invention may include any of the following biodegradable polymers, alone or in combination: poly($\alpha$-hydroxy acids), such as, polycapro lactone (PCL), poly(lactide-co-glycolide) (PLGA), polylactide (PLA), and polyglycolide (PGA), and combinations and blends thereof above at different ratios to fine-tune release rates, PLGA-PEG (polyethylene glycol), PLA-PEG, PLA-PEG-PLA, polyanhydrides, trimethylene carbonates, polyorthoesters, polyaspirins, polyphosphagenes, and tyrozine polycarbonates; natural and synthetic hydrogel materials, e.g., collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, and PLGA-PEO-PLGA. Polymer matrices according to embodiments of the present invention may include any of the following biostable polymers, alone or in combination: polyurethanes, polymethylmethacrylates copolymers, polyvinyl acetate (PVA), polyamides, and copolymers of polyurethane and silicone.

An embodiment according to the present invention includes a process for making a zeolite drug eluting coating. In an embodiment, zeolite drug reservoirs are dispersed within a polymer by mechanical means, for example, by high shear mixing with a dual screw compounder. A coating solution may then be prepared by contacting the polymer containing the dispersed zeolite particles with an appropriate solvent that will dissolve the polymer. The polymer and zeolite drug reservoir solution may then be applied to a substrate of the medical device by various means known in the art, such as, spraying, dipping, coating, spinning, casting, molding, overlaying and/or any combination of these methods.

It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

The invention claimed is:

1. A medical device having at least one surface for contacting a bodily tissue, organ or fluid, the medical device comprising:
    a substrate having a contacting surface; and
    a drug-eluting coating on at least a portion of the contacting surface, wherein the coating is comprised of a polymer having zeolites dispersed there through and wherein a porous structure of the zeolites includes reservoirs containing a release agent and a therapeutic material.

2. The medical device of claim 1, wherein the release agent prevents the therapeutic material from exiting the reservoir until a triggering condition is met.

3. The medical device of claim 2, wherein the triggering condition is contact of the release agent with a bodily fluid.

4. The medical device of claim 2, wherein the triggering condition is a change in pH proximate the release agent.

5. The medical device of claim 1, wherein the polymer is bioerodible.

6. The medical device of claim 1, wherein the medical device is an implantable medical device.

7. The medical device of claim 6, wherein the implantable medical device is a stent for implanting in a vessel system.

8. A drug-eluting stent for implanting in a body lumen comprising:
    a radially expandable stent structure; and
    a coating on at least a portion of a surface of the stent structure, wherein the coating is comprised of a polymer having zeolites dispersed there through and wherein a porous structure of the zeolites includes reservoirs containing a release agent and a therapeutic material.

9. The stent of claim 8, wherein the reservoirs also contain a release agent for preventing the release of the therapeutic material from the reservoir until a triggering condition is met.

10. The stent of claim 9, wherein the triggering condition is contact of the release agent with a bodily fluid.

11. The stent of claim 9, wherein the triggering condition is a change in pH proximate the release agent.

12. The stent of claim 11, wherein the polymer is a bioerodible polymer having lactic acid as a degradation product for providing the change in pH.

13. The stent of claim 8, wherein the therapeutic material is a pharmaceutical compound.

14. The stent of claim 13, wherein the coating further comprises:
    an outer layer having zeolites containing a first pharmaceutical compound; and
    an inner layer having zeolites containing a second pharmaceutical compound.

15. The stent of claim 14, wherein the outer layer is of a bioerodible polymer and the first pharmaceutical compound is selected from a group consisting of an anti-coagulant drug and an anti-inflammatory drug.

16. The stent of claim 15, wherein the second pharmaceutical compound is selected from a group consisting of an anti-proliferative and a pro-healing agent to promote rapid re-endothelialization.

17. A drug-eluting coating of a medical device, the coating comprising:
    a polymer dispersed with zeolite drug carriers, wherein a porous structure of the zeolite drug carriers includes reservoirs containing a release agent and a pharmaceutical compound.

18. The coating of claim 17, further comprising:
    an outer layer of a bioerodible polymer having zeolite drug carriers with a first pharmaceutical compound; and
    an inner layer of a polymer matrix having zeolite drug carriers with a second pharmaceutical compound.

* * * * *